United States Patent [19]

Thach

[11] Patent Number: 5,342,782
[45] Date of Patent: Aug. 30, 1994

[54] TIGHTLY REGULATED EXPRESSION SYSTEM FOR EUCARYOTIC CELLS

[75] Inventor: Robert E. Thach, St. Louis, Mo.

[73] Assignee: Washington University, St. Louis, Mo.

[21] Appl. No.: 840,767

[22] Filed: Feb. 24, 1992

[51] Int. Cl.$^5$ .............................................. C12N 15/85
[52] U.S. Cl. .................. 435/320.1; 435/69.1; 435/172.1; 435/240.2
[58] Field of Search ................ 435/320.1, 69.1, 172.1, 435/172.3, 252.3; 935/34, 39, 41, 44, 51

[56] References Cited

PUBLICATIONS

Casey et al, EMBO J., 1989, vol. 8, No. 12, pp. 3693–3699.
Walden et al., Gene (1987) 61:317–327.
Lawson et al., J. Virol. (1989) 63(12):5013–5022.
Hentze et al., Science (1987) 238:1570–1573.
Aziz et al., Proc. Natl. Acad. Sci. (1987) 84:8478–8482.
Brown et al., J. Biol. Chem. (1989) 264(23): 13383–13386.
Walden et al., Biochemistry (1986) 25:2033–2041.
Rouault et al., Proc. Natl. Acad. Sci. (1987) 84:6335–6339.

Primary Examiner—Richard A. Schwartz
Assistant Examiner—David Guzo
Attorney, Agent, or Firm—Morrison & Foerster

[57] ABSTRACT

The invention relates to an expression system which permits control of the levels of protein produced, and optionally provides production of the mature form of the protein directly. The expression systems of the invention include the desired gene downstream of a first DNA which comprises the reverse transcript of an inducible translational regulator and a second DNA which is the reverse transcript of an mRNA capable of self-stabilization. This translated sequence is in turn under the control of a transcriptional promoter which may also be inducible. In a preferred embodiment, the inducible translational regulator is the iron responsive element (IRE) region of ferritin mRNA, and the stabilizing element is also a portion of the ferritin sequence. The expression system is useful, especially, for the production of toxic proteins since protein production can be delayed until desired.

10 Claims, 4 Drawing Sheets

TIGHTLY REGULATED EXPRESSION SYSTEM FOR EUCARYOTIC CELLS

This work was performed at least in part under a grant from the U.S. Government. The U.S. Government has certain rights in this invention.

TECHNICAL FIELD

The invention relates to production of recombinant proteins in transformed eucaryotic cells. More specifically, it concerns expression systems for recombinant production which permit regulation of expression so as to obtain this production at times when the cells are able to tolerate enhanced amounts of the recombinant protein.

BACKGROUND ART

A recognized problem in recombinant protein production is the toxicity of foreign proteins to the recombinant host. Desirably, the protein should be produced in large amounts-as much as about 40% of the total production of protein in the cell. However, foreign proteins are inherently aberrant in the host and therefore are often unhealthy for the cells at high concentration levels, even if they are not toxins in the conventional sense.

One approach to mitigating this problem is to delay the production of the desired protein until the cells have achieved a satisfactory level of growth. While the enhanced production at that time may eventually have a morbidity effect on the culture, there are sufficient cells available by the time protein production is induced to supply sufficient yield before morbidity occurs. To effect this delay, conventionally, inducible promoter systems have been employed. In mammalian cells the metallothionein promoter has been most commonly used. "Superinduction" protocols have been devised involving treatment with zinc ion which give a 50-fold induction of the synthesis of human leutropin (Walden, W. E., et al., *Gene* (1987) 61:317–327) or the encephalomyocarditis (EMC) virus 3B and 3C proteins (Lawson, T. G., et al., *J. Virol.* (1989) 63:5013–5022). Considerable cell lysis resulted from these enhanced concentrations of protein. As very high levels of protein production were achieved, an increase in overall yield is achievable only by enhancing the effectiveness of induction. This comprises suppressing both transcription and translation of the transcripts so as to minimize cytotoxicity during clonal selection and cell proliferation phases to enhance the probability of isolating cell lines that can be induced to produce large quantities of the desired protein.

In addition to regulating the production of the protein at the transcriptional level, regulation at the translational level is also known. The mRNA transcript of all ferritins contains a sequence of about 27 to about 60 nucleotides in the 5'-untranslated region which appears to repress translation of the mRNA in the absence of iron; when a source of iron ion is added, translation can go forward. This "iron-responsive element" (IRE) is thought to form a stem-loop structure which is recognized by ferritin repressor protein or "IRE-binding" protein. The function of the iron ion appears to reside in its ability to inactivate the repressor protein (Hentze, M. W., et al., *Science* (1987) 238:1570–1573; Aziz, N., and Munro, H. N., *Proc. Natl. Acad. Sci. USA* (1987) 84:8478–8482; Brown, P. H., et al., *J. Biol. Chem.* (1989) 264:13383–13386).

While the ability of the IRE to control the translation of ferritin so as to permit controlled protein production is established, this translation regulator does not seem to be effective with respect to all coding sequences contained in the mRNA. It has now been found that the combination of an inducible translation regulator such as IRE with a message-masking element (MME) results in a dependable translation regulation system which permits control of recombinant protein expression. This combination, when further used in conjunction with a transcription regulator, results in an approximately 500-fold induction for most proteins.

DISCLOSURE OF THE INVENTION

The invention is directed to DNA constructs and host expression vectors which permit the controlled production of recombinant proteins at high levels, even though these proteins may be toxic to the host cells. The system comprises a transcriptional promoter operably linked to two DNA sequences which regulate translation. The first DNA sequence is the reverse transcript of an inducible translational regulator; the second DNA sequence is the reverse transcript of an RNA effective in stabilizing the RNA of which it is a part and further containing a coding sequence overlapping at least a portion of the stabilizing RNA.

Thus, in one aspect, the invention is directed to a DNA construct for the expression of a desired gene which comprises a transcriptional promoter operably linked to the above-referenced first and second DNA sequences, wherein the second sequence is operably linked to a third DNA sequence comprising the coding region of the desired gene.

In another aspect, the invention is directed to host expression vectors which contain the foregoing control elements but, rather than the desired gene, contain a polylinker region containing restriction sites to permit the insertion of the DNA encoding any other desired protein in reading frame with the translatable portion of the second DNA.

In other aspects, the invention is directed to cells transformed with the expression construct of the vector and to methods to produce desired proteins by culturing the transformed cells under conditions wherein transcriptional and translational expression are induced.

In a preferred embodiment, the invention is directed to the expression systems of the invention wherein the desired protein is contained in a viral genome in a manner that will effect the excision of the desired protein by means of an encoded protease.

MODES OF CARRYING OUT THE INVENTION

Figure 1:
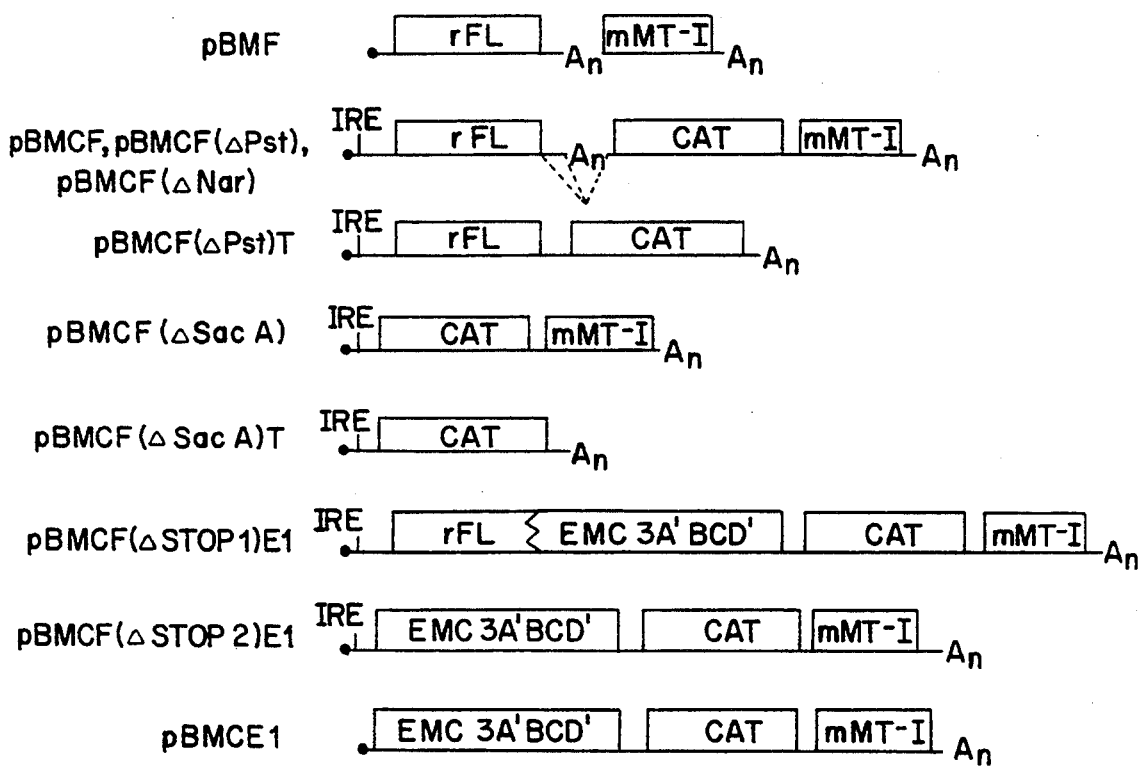
FIG. 1 shows the mRNA encoded by the various vectors illustrated below.

The constructs useful in the invention contain at least a first and second DNA sequence, each of which is a reverse transcript of an RNA that directly or indirectly controls translation. The first DNA sequence is the reverse transcript of an inducible translation regulator. By "inducible translation regulator" is meant an RNA sequence which permits the translation of the downstream portions of the mRNA on which it is contained only in the presence of inducing conditions. Absent the conditions of induction, the inducible translation regulator prevents the translation of the downstream coding sequence. Illustrated herein is the iron-responsive element (IRE) which is present in the mRNAs which encode all of the ferritins. This IRE is induced in the presence of iron ion. As set forth in the Background section above, the ferritin-derived IRE comprises an approximately 27–60 nucleotide sequence that binds to a repressor protein in the absence of a source of iron ion. When iron ion is present, the repressor protein no longer binds the IRE, and the translation is de-repressed. The de-repression is believed to occur through the inactivation of the repressor protein.

The second translation regulator which is provided for in the expression systems of the invention is an mRNA element that stabilizes the RNA in which it is contained and protects it from degradation—i.e., a "stabilizing element." This element is typically located 1–10,000 bases, more preferably 1–1000 bases, downstream of the inducible translation regulator and contains at least a portion which is in open reading frame with respect to the mRNA encoding the protein whose production is desired. Illustrated herein is the message-masking element (MME) of the ferritin gene. This stabilizing element may include a portion of the 5'- untranslated region, but certainly includes a portion of the coding sequence for the ferritin gene. As a portion of the ferritin coding sequence is included, the coding portion must be in open reading frame with the RNA encoding the desired protein.

Thus, in the construction of the DNA-containing vector, this second DNA, which represents a reverse transcript of the stabilizing element RNA, will be inserted downstream of the first DNA sequence, and the relevant coding sequence portion will be in open reading frame with the open reading frame of the desired gene. Other translational regulatory elements which stabilize the mRNA in which they are contained include the IREs in the 3' UTR of the transferrin receptor mRNA (Mullner, et al., *Cell* (1989) 58:373–382; Casey, et al., *EMBO J.* (1989) 8:3693–3699.

The MME can also be made to function outside of any open reading frame. For example, all of the AUG codons within the ferritin open reading frame may be mutated to non-initiating codons without destroying the function of the MME (e.g., positions 102, 226, 306, 364, 390, 445, and 534 of the rabbit ferritin light chain cDNA; see Daniels-McQueen, et al., Nucleic Acids Research (1988) 16:7741).

The DNA constructs of the invention must also, of course, contain transcriptional controls. While any transcriptional promoter can be used, it is preferable to provide an inducible promoter, since the induction effect on transcription is expected to be a multiple of that effected by the translational regulation. Suitable inducible promoters operable in eucaryotic cells include the metallothionein promoter (which can be induced with a wide variety of agents, including zinc or cadmium, and for which superinduction protocols have been devised), the heat shock promoter, and the mouse mammary tumor virus long terminal repeat. Choice of the transcriptional promoter will, of course, depend on the choice of eucaryotic host cell.

The eucaryotic host cells appropriate for use in the invention include, preferably, vertebrate cells and, more preferably, mammalian cells. Murine cell lines are especially preferred. However, in addition, other eucaryotes such as yeast cells may also be employed.

The elements of the expression system are constructed using standard recombinant DNA techniques. The transcriptional promoter is upstream of and operably linked to the first and second DNA sequences, which are reverse transcripts of the inducible translation regulator and the RNA stabilizing sequence, respectively. By "operably linked" is meant that the elements are ligated in such a fashion that their intended functions may be fulfilled. Thus, the promoter "operably linked" to the first and second DNA sequence is ligated in such a position and manner as to be capable of effecting the transcription of these DNAs into mRNA. The inducible translation regulator is positioned in the 5'-untranslated sequence of the mRNA and is thus upstream of the RNA stabilizing element. It functions most effectively when close (approximately 28 nucleotides) to the 5' cap. Accordingly, the DNA which represents its reverse transcript is ligated just downstream of the transcription initiation site (indeed, the transcription initiation site is conveniently introduced as part of the first DNA) and upstream of the RNA stabilizing element. The two DNA sequences are proximal to each other and can also be introduced as a unit, for example, as illustrated below, as a segment of the ferritin light-chain gene. As the second DNA includes a portion of coding sequence, this coding sequence should be ligated in reading frame with the coding sequence for the desired protein.

Typically a host expression vector is constructed which includes the transcription promoter operably linked to the first and second DNAs which are reverse transcripts of the translation regulating RNAs (i.e., the inducible translation regulator and the stabilizing element) followed by a polylinker sequence to permit in-frame insertion of the DNA encoding the desired protein, optionally followed by termination control sequences such as polyadenylation sites and transcription terminator sequences. These termination controls can be supplied from appropriate host sources such as those that control the termination of transcription of eucaryotic mRNAs such as SV40 mRNAs. Care must be taken in the choice of such termination controls as some controls are known to contain sites for nuclease degradation, such as in the metallothionein gene itself.

Typical polylinker sequences for gene insertion can be constructed synthetically and will include a variety of restriction sites. A useful polylinker region is that described by Lawson, T. G., et al., *J. Virol.* (1989) 63:5013–5022, cited above. This polylinker contains BssHII, SalI, EcoRV, ApaI and XhoI, in two orientations. Alternatively, the coding sequence can be directly engineered by ligation to the second DNA sequence that represents the reverse transcript of the stabilizing element using a restriction site internal to the stabilizing element reverse transcript DNA. Techniques for modifying the termini to assure reading frame ligation are well known in the art.

A particularly preferred system for production of a desired protein takes advantage of the ability of the inducible expression system of the invention to produce proteins representing those encoded by the EMC virus genome. Thus, the portion of the genome designated 3A'BCD' putatively produces a fusion protein which includes a part of the 3A peptide (3A'), the complete 3B peptide sequence, the complete 3C peptide sequence, and a portion of the 3D sequence designated 3D' (see Lawson, et al., supra). As the 3C peptide is a protease, foreign genes inserted in reading frame in, for example, the 3B region, or following the 3D' region, will be cleaved to obtain mature proteins. Thus, appending the desired coding sequence onto that of 3D' results in the production of the mature protein with only a short additional peptide appended to the N-terminus.

The expression vectors constructed according to the method of the invention are transfected or transformed into suitable recombinant host cells which are then cultured under conditions which permit the regulated production of the desired protein. The choice of host will depend on the nature of the transcription and translation-regulating elements selected for the expression system. Typically, the transfected cells are cultured under conditions where expression is repressed until a high density of cells is achieved. Then conditions appropriate for the induction of expression are superimposed on the culture and protein production is commenced. The protein produced is then recovered either from the supernatant or by cell lysis and purified using conventional means. A wide variety of proteins can be produced in this manner and recovered for use in therapy, diagnosis, industrial processes, and the like.

The following examples are intended to illustrate but not to limit the invention.

EXAMPLE 1

Construction of Expression Vectors and Transfection of Host Cells

Expression vectors were constructed as outlined in FIG. 1. All are modified forms of the plasmid pBMF which is described by Walden, W. E., et al., *Gene* (1987) 61:317-327, cited above. This plasmid contains sequences encoding the ferritin light chain (rFL) and sequences encoding murine metallothionein-I (mMT-I) separately initiated and terminated and both under control of the murine metallothionein promoter. The DNA which is the reverse transcript of the IRE discussed above is not included. This vector and the derivative vectors described herein are suitable for transfection into murine host cells.

As shown in FIG. 1, the following modifications to pBMF were made. First, the series designated pBMCF and related designations include the insertion of the sequences encoding the chloramphenicol acetyl transferase (CAT) gene downstream from the rFL open reading frame (ORF). The CAT ORF is illustrative of the desired coding sequence; according to the scanning hypothesis this gene should be translationally regulated in a manner comparable to that of the rFL upstream open reading frame (Kozak, M., *Mol. Cell Biol.* (1987) 7:3438-3445). In pBMCF itself, the reverse transcript of the IRE is included upstream of the rFL open reading frame and the CAT open reading frame is separately initiated downstream. The genomic form of the mMT-I open reading frame, which contains two introns, is also included. In the family of vectors shown in FIG. 1, the corresponding pBMCF(ΔPst) and pBMCF(ΔNar) contain deletions downstream of the PstI and NarI sites respectively (see Daniels-McQueen, S., et al., *Nucleic Acids Res.* (1988) 16:7741), so that the ΔPst vector lacks the poly-A region and the ΔNar vector lacks both the poly-A and the 3' untranslated region of the rFL mRNA. These plasmids are grouped in FIG. 1 as they behaved similarly with respect to expression.

A second modified vector, designated pBMCF(ΔSacA) deletes the coding sequences for rFL and places the CAT gene directly under control of the promoter and also includes the upstream IRE sequence. This vector is constructed by cleaving at the second SacII site and deleting the regions downstream from the cleavage site.

A third series of modified vectors designated pBMCF(ΔSacA)T and pBMCF(ΔPst)T results from excising the coding sequences for mMT-I by inserting an SV40 transcriptional termination signal between the CAT and mMT-I ORFs.

The next series of vectors contains the EMC viral genome region 3A'BCD'. pBMCF(Δstop1)E1 contains both of the translational regulators inherent in the ferritin mRNA message. This series of vectors encodes an mRNA which includes the IRE and the MME described above in reading frame with the EMC-derived coding sequences. This vector further contains reading frames for CAT and mMT-I, as do the pBMCF(Δstop2-)E1 and pBMCE1. However, pBMCF(Δstop2)E1 lacks the MME region of the ferritin mRNA; pBMCE1 also lacks the IRE region.

In all of the foregoing constructs, transcription starts at the mMT-I cap site and ends at the mMT-I or SV40 transcription termination site. Those vectors which contain the IRE and MME of the ferritin message have 5'-untranslated regions of approximately 213 nucleotides containing a 28 nucleotide IRE sequence that starts at nucleotide 47. The start of the ferritin light chain open reading frame is at nucleotide 214; if the entire light chain coding sequence is contained, the stop codon is at nucleotide 739. The PstI and NarI sites used to delete the internal poly-A and the internal poly-A plus the 3'-untranslated region, respectively, are at nucleotides 863 and 746. The SacII site used in constructing pBMCF-(ΔSacA), pBMCF(ΔSacA)T, and pBMCF(Δstop2)E1 is at nucleotide 144. The total length of the messages encoded by the plasmids shown in FIG. 1 are 1300, 2200, 2045, 1920, 1795, 1300, 1050, 2750, 2190, and 2045 nucleotides respectively.

The vectors constructed above are transfected into mouse C127 cells which had been maintained in Dulbecco's Modified Eagle's Medium supplemented with 10% heat-inactivated fetal bovine serum as described by Howley, P. M., et al., *Methods Enzymol.* (1983) 101:387-404. The cells were cotransfected with the desired plasmid and pSV2-neo according to the calcium precipitation method. Clones resistant to G418 were selected and lysates from these clones were prepared by freeze-thawing cells three times in 0.25M Tris HCl pH 7.5 for analysis.

For expression, the cells were cultured and then plated at a concentration of $2 \times 10^5$ cells/ml in Costar 6-well dishes (9 cm$^2$/well) in Earle's MEM containing 2% serum. Various induction conditions were used.

For superinduction, after 42 hr, the cells are treated with 30 μM zinc sulfate plus 1 μg/ml cycloheximide for 6 hr. The media were removed and cells were washed three times with Earle's Basal Salt Solution. Fresh media were added containing either 1 μg/ml of actinomycin D or 1 μg/ml of actinomycin D plus 100 μM ferric ammonium citrate in 0.2 mg/ml transferrin. Heme, at a concentration of 10-50 μM, may be substituted for ferric ammonium citrate plus transferrin. In labeling experiments, after 4 hr, the cells were labeled as described in Lawson, et al. (1989), supra.

EXAMPLE 2

Expression Characteristics of Vectors Containing an Inducible Translation Regulator and a Stabilizing Element The series represented by pBMCF(ΔPst) was tested for expression as described in Example 1. This vector produces an mRNA that contains both the IRE and MME; the MME is partially or wholly included in the ORF for the rFL; the CAT sequences are in a downstream ORF.

After induction, the cells were pulse-labeled with $^{35}$S-methionine for 2 hr, then lysed and labeled proteins were analyzed by SDS-PAGE gel electrophoresis followed by fluorography. Fluorography was conducted by the Apex method of Jen and Thach (*J. Virol.* (1982) 43:250–261) or with Amplify (Amersham) and exposed to preflashed Kodak X-Omat film at −70° (Laskey, R. A., *Meth. Enzymol.* (1980) 65:363–371).

Various induction protocols were employed:
1) no treatment;
2) 100 μM $Fe^{+3}$ as ferric ammonium citrate+0.2 mg/ml transferrin (Tf) for 4 hr;
3) desferal (desferioxamine mesilate) for 16 hr;
4) desferal for 16 hr followed by iron $Fe^{+3}$+Tf for 4 hr;
5) 30 μM $Zn^{+2}$ (zinc sulfate) for 6 hr;
6) $Zn^{+2}$ for 6 hr followed by $Fe^{+3}$+Tf for 4 hr;
7) $Zn^{+2}$+1 μg/ml cycloheximide for 6 hr followed by 2 μg/ml actinomycin D; and
8) $Zn^{+2}$+cycloheximide for 6 hr followed by actinomycin D+$Fe^{+3}$+Tf for 4 hr.

Labeled ferritin was detectable only under induction protocols 7 and 8 which involve superinduction with $Zn^{+2}$ and cycloheximide. However, when the additional induction using $Fe^{+3}$+Tf was also employed in induction protocol 8, a much higher amount of ferritin was detected. Quantitation showed that there was a 200-fold induction of ferritin synthesis relative to uninduced control using the combination of zinc/cycloheximide superinduction with $Fe^{+3}$/Tf/actinomycin D induction.

Despite the 200-fold enhancement of ferritin production no CAT protein was detected on the gels.

The production of the ferritin protein was relatively stable over time and was readily detected after 20 hr. In experiments similar to those described above, the cells were pulse-labeled with $^{35}$S-methionine from 4–5 hr and from 19–20 hr after transfer from the $Zn^{+2}$+cycloheximide to actinomycin D in the presence of $Fe^{+3}$+Tf. SDS-PAGE and fluorography showed the presence of considerable amounts of ferritin under these conditions.

As CAT protein production was not detected, Northern blots to assess transcript structure and stability were performed. The cells were superinduced with $Zn^{+2}$+cycloheximide for 6 hr and then further treated with $Fe^{+3}$+Tf+actinomycin D, or with actinomycin D alone for 0–6 hr. The cells were then lysed and the RNA was extracted with phenol+chloroform, precipitated with ethanol and ammonium acetate and subjected to Northern blot analysis, using as probe a labeled transcript complementary to 267 nucleotides in the CAT open reading frame. The presence of CAT sequences was clearly shown.

Thus, although it appeared that the complete mRNA shown in FIG. 1 was transcribed, and the mRNA was sufficiently stable to be detected in Northern blot analysis, the CAT sequences were apparently not translated. Only the first ORF was translated, not a second ORF immediately downstream.

However, increasing the sensitivity of the assay for translation product by employing immune precipitation with anti-CAT antibody prior to SDS-PAGE and fluorography permitted detection of CAT protein produced from pBMCF(ΔPst). Quantitation showed that CAT synthesis is about 600-fold lower than synthesis of the ferritin light chain. Induction by iron had little effect on the levels of CAT produced.

EXAMPLE 3

Effect of Deletion of the Stabilizing Element

The levels of CAT obtained could be enhanced by deletion of the upstream ferritin light chain coding sequences in the vector pBMCF(ΔPst), to create a new vector, pBMCF(ΔSacA). Detectable levels of CAT under all conditions could be obtained using this vector; these levels were somewhat increased by the induction with $Fe^{+3}$/Tf.

Because it is known that metallothionein mRNA is degraded about 8 hr after the start of induction by cadmium (Enger, M. D., et al., *Nucleic Acids Res.* (1979) 7:271–288), pBMCF(ΔSacA)T which deletes the mRNA sequences corresponding to mMT-I was constructed. The effect of $Fe^{+3}$/Tf/ActD induction in this vector was more pronounced.

Figure 2:
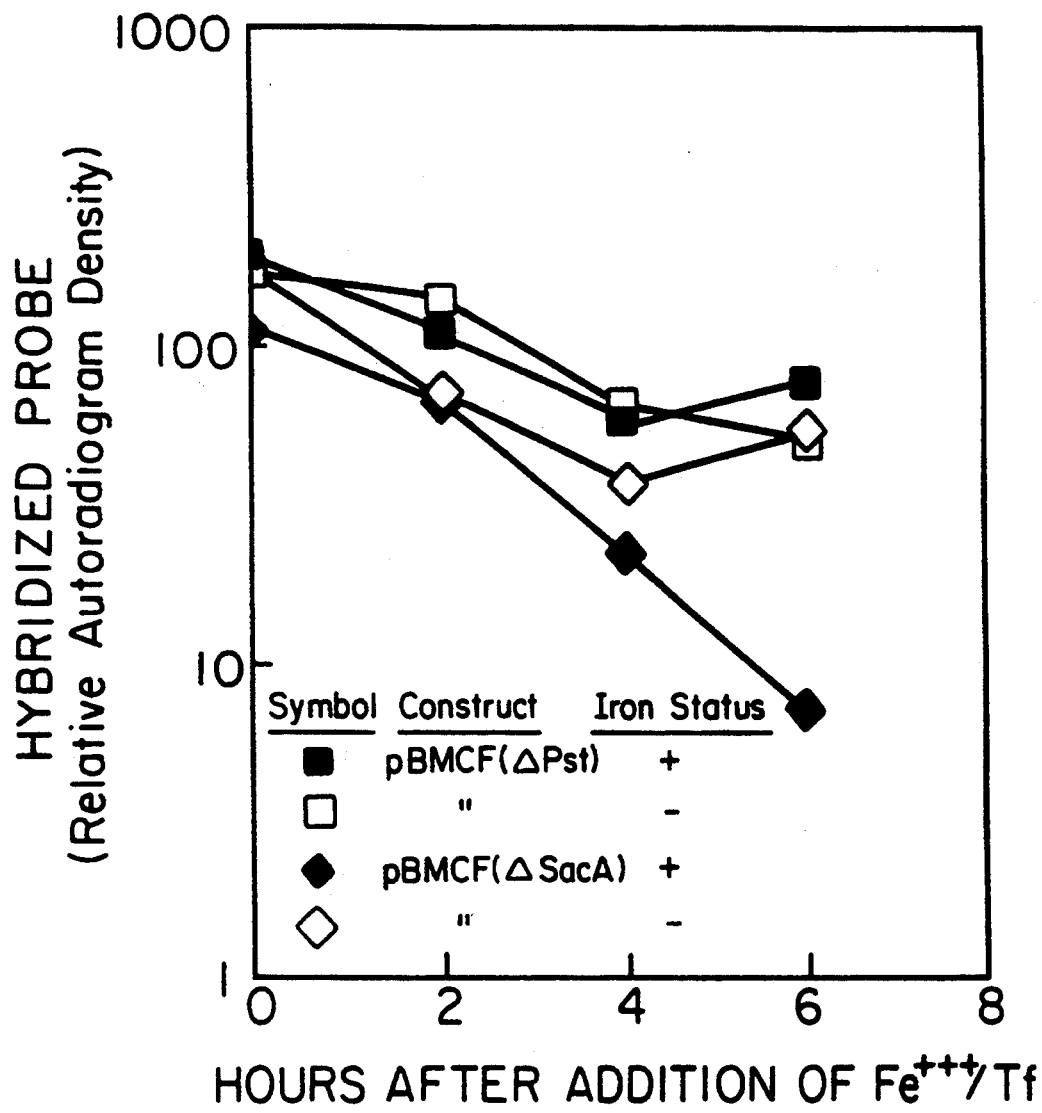
FIG. 2 shows the levels of mRNA as a function of time in cells transfected with pBMCF(ΔPst) as compared to pBMCF(ΔSac-A).

The mRNA stability in cells transformed by pBMCF(ΔPst) or pBMCF(ΔSacA) was directly analyzed as a function of time using Northern analysis as described above with the complementary CAT probe. The results of this analysis are shown in FIG. 2 with and without induction using iron. As shown in FIG. 2, the mRNA levels for the vectors containing the rFL open reading frame are stable over 6 hr after the addition of $Fe^{+3}$+Tf; if the iron induction is omitted, the mRNA derived from pBMCF(ΔSacA) is also stable. However, when induced with iron, the message is degraded.

Figure 3:
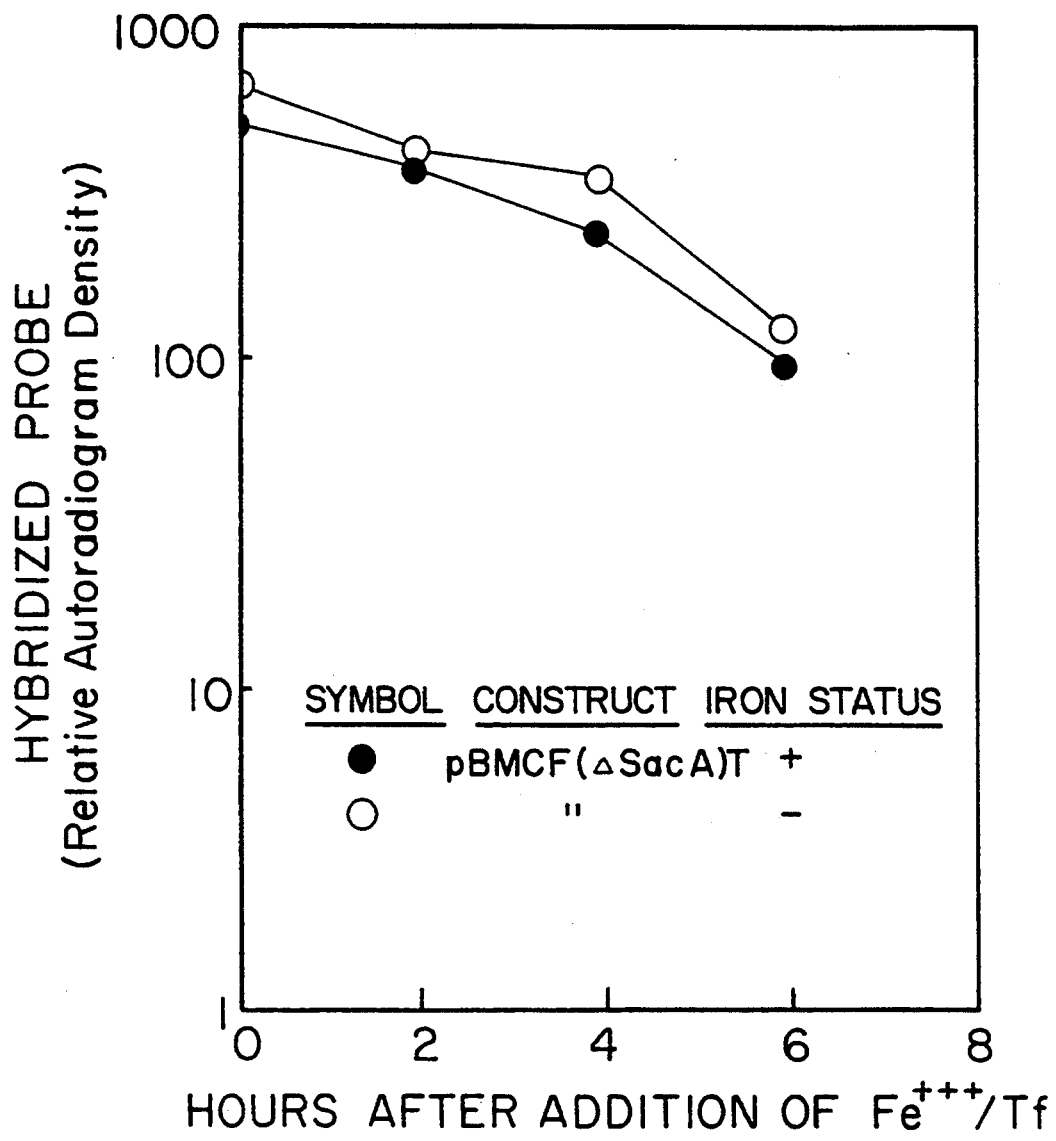
FIG. 3 shows the levels of mRNA as a function of time in cells transfected with pBMCF(ΔSac-A)T.

On the other hand, message produced by pBMCF-(ΔSacA)T which lacks the mMT-I RNA is comparatively stable, as shown in FIG. 3, in both the presence and absence of $Fe^{+3}$/Tf. Although the message is more stable than that generated by pBMCF(ΔSacA) the mRNA level does degrade over time. As there is no difference in stability in the presence and absence of iron, the inducibility of CAT synthesis in the presence of iron is greatly improved and a 6-fold derepression of translation by $Fe^{+3}$/Tf is obtained.

Figure 4:
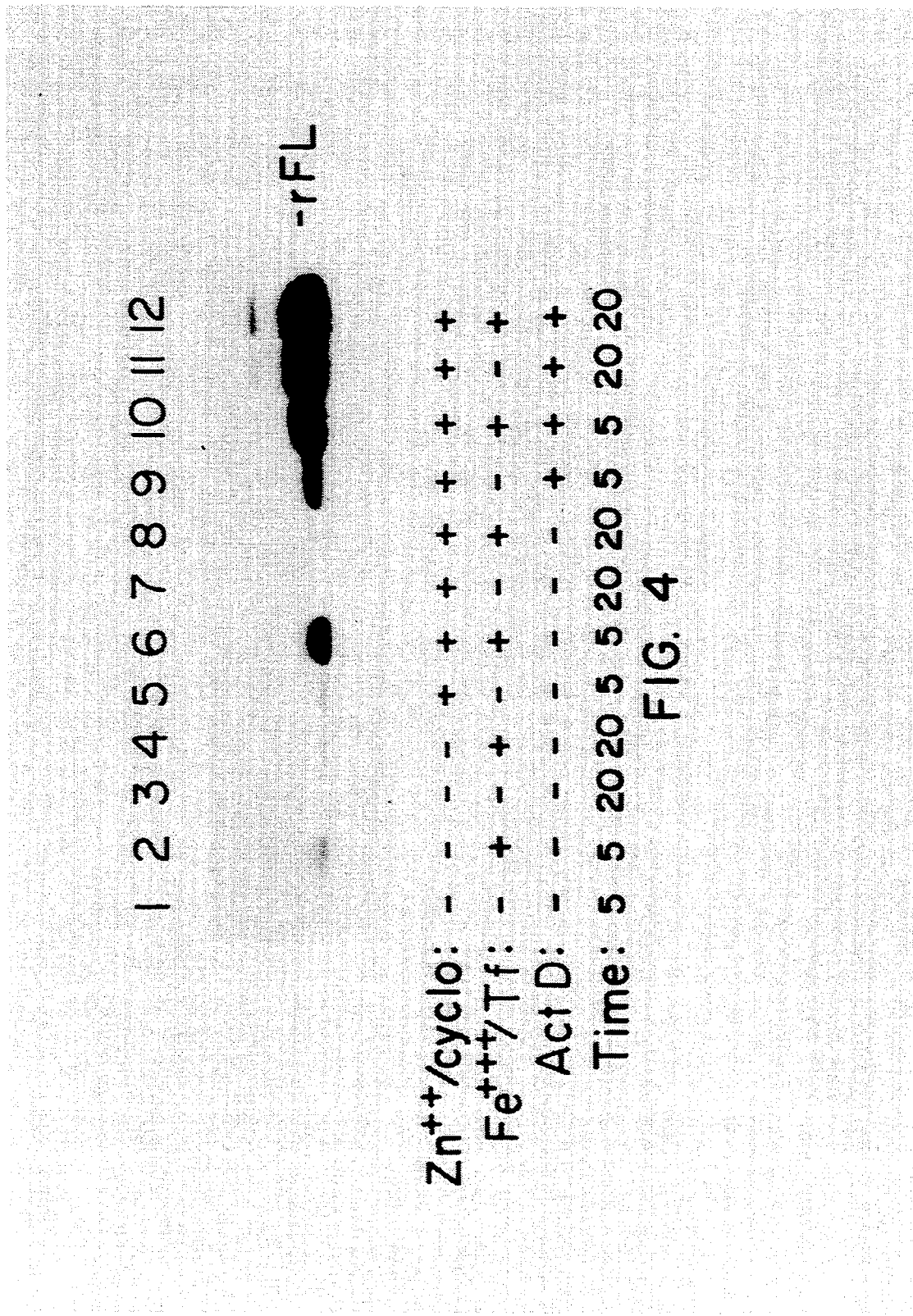
FIG. 4 is a photocopy of a gel showing the levels of recombinant ferritin light chain produced by cells transfected with pBMCF(ΔPst)T.

A similar positive effect of deleting the mMT-I region from the mRNA was detected in the vector pBMCF(ΔPst)T which is similar to pBMCF(ΔSacA)T but constructed from pBMCF(ΔPst). The cells were induced as described above and pulse-labeled with $^{35}$S-methionine for 1 hr either 4 or 19 hr after transfer from the superinduction protocol and analyzed for ferritin produced. High levels of production were maintained even after 20 hr when iron induction was employed as shown in FIG. 4. Indeed, the theoretical 500-fold induction after 20 hr was achieved with this construct.

EXAMPLE 4

Expression of Foreign DNA in the Presence of Inducible Translation Regulator and Stabilizing Element The vector pBMCF(Δstop1)E1 contains both the IRE and MME derived from ferritin wherein the downstream sequences of the MME are in reading frame with the reporter gene EMC 3A'BCD'. The EMC viral 3A'BCD' mRNA is known to be very unstable with or without metals with a half-life of less than one hr (Lawson 1989, supra). pBMCF(Δstop2)E1 and pBMCE1 were used as controls.

The cells were superinduced by protocol 8 above except that 20 μM hemin was used in place of $Fe^{+3}$/Tf. The proteins were pulse-labeled with $^{35}$S-methionine from 4–5 hr after transfer from $Zn^{+2}$+cycloheximide into $Fe^{+3}$/Tf/ActD. The protein was detected as appropriate by precipitation with anti-CAT antibody or with a mixture of antibodies raised against EMC 3A' 3B, 3C, and 3D' regions. The results were assessed by SDS-PAGE and fluorography.

For pBMCF(Δstop1)E1, production of the ferritin-3A' fusion peptide is induced approximately 200-fold, but CAT synthesis is reduced even with respect to that obtained by pBMCF(Δstop2)E1. On the other hand, in the absence of the MME ferritin sequences in pBMCF(Δstop2)E1, synthesis of EMC 3A' is reduced. The stability of mRNA in cells transformed by pBMCF(Δstop1)E1 and pBMCE1 was compared by assessing the rate of translation maintained over 5 hr. The cells were pulse-labeled with $^{35}$S-methionine from 0–1 or 4–5 hr (when $Fe^{+3}$/Tf was used) or 2–3 hr (when 20 μM hemin was used) after transfer from $Zn^{+2}$/cycloheximide to ActD. The labeled proteins were immune precipitated with anti-EMC antibodies and analyzed with SDS-PAGE and fluorography as set forth above. Only pBMCE1 produced detectable amounts of CAT.

Although the preferred embodiments have been described in some detail, it is understood that obvious variations can be made without departing from the spirit and scope of the invention as defined by the appended claims.

I claim:

1. A DNA construct for the expression of a desired non-ferritin gene, which construct comprises a transcriptional promoter operably linked to a first DNA sequence which is the reverse transcript of an inducible translational regulator, which regulator is the iron-responsive element (IRE) region of ferritin light-chain mRNA, and which first DNA is operably linked to a second DNA sequence which is a reverse transcript of a stabilizing element, said stabilizing element being the message-masking element (MME) of the ferritin light-chain mRNA and said second DNA sequence being operably linked to a third DNA sequence comprising the coding region of the desired gene, wherein said gene encodes chloramphenicol acetyl transferease (CAT) or wherein said gene is the portion of the Encephalomyocarditis virus genome designated 3 A'BCD'.

2. The construct of claim 1, wherein the downstream portion of said second DNA sequence is in open reading frame with the third DNA sequence.

3. The construct of claim 1 wherein the transcriptional promoter is inducible.

4. The construct of claim 3 wherein the promoter is the metallothionein promoter.

5. A recombinant host mouse cell transfected with the construct of claim 1.

6. The construct of claim 2 wherein the open reading frame encodes a protease cleavage site.

7. The construct of claim 6 wherein the protease cleavage site is cleavable by a viral protease, and wherein said construct further includes, in open reading frame with the desired gene, a viral protease-encoding DNA.

8. The construct of claim 7 wherein said protease is an EMC viral protease.

9. The construct of claim 8 wherein said desired gene is included within the 3B region or follows the 3C region of the EMC genome and wherein said construct further includes at least a portion of the 3A region, the 3C region and a portion of the 3D region.

10. A DNA vector for the expression of a desired gene, which vector comprises a transcriptional promoter operably linked to a first DNA sequence which is the reverse transcript of an inducible translational regulator, which regulator is the iron-responsive element (IRE) region of ferritin light-chain mRNA which first DNA sequence is operably linked to a second DNA sequence which is a reverse transcript of a stabilizing element, which element is the message-masking element (MME) of ferritin light-chain mRNA and said second DNA sequence being followed downstream thereof with restriction sites that permit insertion of said desired gene in open reading frame with the transcript of said second DNA, said restriction sites not being endogenous to the ferritin gene.

* * * * *